(12) United States Patent
Hoyte et al.

(10) Patent No.: US 8,424,292 B2
(45) Date of Patent: Apr. 23, 2013

(54) SYSTEMS AND APPARATUS RELATING TO THE MONITORING AND/OR CONTROLLING OF SELECTIVE CATALYTIC REDUCTION PROCESSES

(75) Inventors: Scott M. Hoyte, Fountain Inn, SC (US); Vivek V. Badami, Schenectady, NY (US); Chayan Mitra, Karnataka (IN); Ayan Banerjee, Kalyani (IN)

(73) Assignee: General Electric Company, Schenectady, NY (US)

( * ) Notice: Subject to any disclaimer, the term of this patent is extended or adjusted under 35 U.S.C. 154(b) by 633 days.

(21) Appl. No.: 12/650,825

(22) Filed: Dec. 31, 2009

(65) Prior Publication Data
US 2011/0154806 A1    Jun. 30, 2011

(51) Int. Cl.
*F01N 3/00* (2006.01)
(52) U.S. Cl.
USPC ............... 60/286; 60/275; 60/276; 60/301; 60/303; 73/23.2; 73/23.31; 73/23.37
(58) Field of Classification Search .......... 60/274, 60/275, 276, 277, 286, 297, 301, 303; 73/23.2, 73/23.31, 23.37
See application file for complete search history.

(56) References Cited

U.S. PATENT DOCUMENTS

| | | | |
|---|---|---|---|
| 6,593,573 B1 | 7/2003 | McCann et al. | |
| 6,721,649 B2 * | 4/2004 | Knott et al. | 701/114 |
| 6,968,679 B2 * | 11/2005 | Pott | 60/285 |
| 7,084,963 B2 * | 8/2006 | Leipertz | 356/73 |
| 7,526,950 B2 * | 5/2009 | Van Nieuwstadt et al. | 73/114.75 |
| 7,936,460 B2 * | 5/2011 | Iwase et al. | 356/438 |
| 2006/0176486 A1 | 8/2006 | Ho | |
| 2011/0239629 A1 * | 10/2011 | Tanoura et al. | 60/276 |
| 2011/0252771 A1 * | 10/2011 | Fujinaga et al. | 60/295 |

FOREIGN PATENT DOCUMENTS

| | | |
|---|---|---|
| EP | 1965194 A1 | 9/2008 |
| WO | 2004090496 A2 | 10/2004 |

OTHER PUBLICATIONS

EP Search Report and Written Opinion issued in connection with corresponding EP Application No. 10195950.0, Apr. 5, 2011.

* cited by examiner

*Primary Examiner* — Binh Q Tran
(74) *Attorney, Agent, or Firm* — Mark E. Henderson; Ernest G. Cusick; Frank A. Landgraff

(57) ABSTRACT

A system for the monitoring and/or controlling emission levels of nitrogen oxide and a reductant from a stream of combustion exhaust, wherein the internal combustion engine includes a SCR unit disposed in the stream of combustion exhaust between an upstream conduit and a downstream conduit, the SCR unit having a catalyst that is configured to catalytically reduce nitrogen oxides contained in the combustion exhaust to elemental nitrogen in the presence of a reductant and oxygen, and wherein the internal combustion engine further includes a reductant injector; the system comprising: a laser absorption spectroscopy unit that is disposed in the downstream conduit and configured to measure the concentration level of at least nitrogen oxide and the reductant in the exhaust; and a control unit.

23 Claims, 6 Drawing Sheets

SYSTEMS AND APPARATUS RELATING TO THE MONITORING AND/OR CONTROLLING OF SELECTIVE CATALYTIC REDUCTION PROCESSES

BACKGROUND OF THE INVENTION

This present application relates generally to methods, systems, and apparatus for monitoring the performance of selective catalytic reduction processes through specie and/or temperature mapping so that the emissions relating to internal combustion engines may be better monitored and/or controlled. More specifically, but not by way of limitation, the present application relates to methods, systems, and apparatus pertaining to performance monitoring of selective catalytic reduction processes through specie and temperature mapping using laser absorption spectroscopy and related processes.

A significant issue related to the use of industrial and utility boiler systems, gas turbine engines, and other internal combustion engines is the amount of nitrogen oxides (or "NOx") that is released into the atmosphere. As a way to combat this problem, many operators for years have used selective catalytic reduction (or "SCR") processes to reduce NOx emissions.

As a result, it will be appreciated that selective catalytic reduction processes, as they relate to reducing NOx emissions, are important for protecting and promoting public health. One reason for this is that NOx, when released into the atmosphere, often mixes with other compounds to create smog, which, of course, is a significant form of air pollution in many cities. Accordingly, the Environmental Protection Agency (or "EPA") sets limits as to the amount of NOx that a facility can legally release into the atmosphere. In order to avoid fines and other penalties, companies that operate such facilities monitor closely and attempt to limit the amount of NOx that is released into the atmosphere.

In general, selective catalytic reduction works by converting nitrogen oxides into diatomic nitrogen (or "$N_2$") and water (or "$H_2O$"), both of which are harmless and safe for the environment when released into the atmosphere. This chemical reaction (i.e., the conversion of NOx into $N_2$ and $H_2O$) is brought about by combining NOx with a reductant, typically ammonia (or "$NH_3$"), which then comes in contact with the catalyst to produce the reaction that separates the NOx into $N_2$ and $H_2O$. When the internal combustion engine, for example, a gas turbine engine, is operating under steady conditions, SCR systems generally prove very effective at reducing the amount of NOx released. For example, in some applications, NOx emissions may be reduced by up to 90%.

However, during transient operating conditions, for example, engine start-up or load swing conditions, NOx output may spike, which may result in excess NOx (beyond acceptable limits) being released into the atmosphere. Further, in attempting to neutralize these raised levels, conventional systems often over-inject ammonia (i.e., inject an excess amount of ammonia) into the selective catalytic reduction system. This, which is generally referred to as $NH_3$ "slippage", leads to an equally troubling situation: the release of unacceptably high levels of $NH_3$ into the atmosphere, which may also occasion fines and other penalties against the operator of the combustion engine.

The reasons conventional systems have such difficulty in regulating NOx and $NH_3$ emission levels during transient conditions generally relate to the limitations associated with certain system components, particularly, with the measuring devices used to determine the concentration levels of the relevant compounds in the exhausts, as well as the limiting configuration of the system. These limitations are many. First, gas composition and specie concentration levels are generally measured through time-consuming extractive technologies using heated sample lines. This is a slow process with lag times of many minutes (and, in some cases, hours) and often delivers unreliable results. Second, conventional systems generally lack temperature data in the measurement location. As $NH_3$ absorption rates are dependent on temperature, this data is necessary for precise control of the process. Third, conventional systems lack information regarding the spatial distribution of the relevant compounds through the exhaust. Fourth, conventional systems generally only measure gas composition downstream of SCR.

It will be recognized that, ideally, specific molar match of ammonia to NOx is highly desirable. When this is the case, NOx emissions are reduced as intended while no or little excess ammonia is released into the atmosphere. In practice, as one of ordinary skill in the art will appreciate and for the reasons provided above, this aim has proved to be difficult to achieve. As a result, there is a continuing need for improved methods, systems, and apparatus relating to the monitoring and/or control of selective catalytic reduction processes.

BRIEF DESCRIPTION OF THE INVENTION

The present application thus describe a system for the monitoring and/or controlling emission levels of nitrogen oxide and a reductant from a stream of combustion exhaust from an internal combustion engine, wherein the internal combustion engine includes a selective catalytic reduction unit disposed in the stream of combustion exhaust between an upstream conduit that directs the stream of combustion exhaust to the selective catalytic reduction unit and a downstream conduit that directs the stream of combustion exhaust away from the selective catalytic reduction unit, the selective catalytic reduction unit having a catalyst that is configured to catalytically reduce nitrogen oxides contained in the combustion exhaust to elemental nitrogen in the presence of a reductant and oxygen, and wherein the internal combustion engine further includes a reductant injector that injects the reductant into the flow of combustion exhaust upstream of the selective catalytic reduction unit, the system comprising: a laser absorption spectroscopy unit that is disposed in the downstream conduit and configured to measure the concentration of at least nitrogen oxide and the reductant in the stream of combustion exhaust; and a control unit. The laser absorption spectroscopy unit may be configured to provide timely data to the control unit relating to the measured concentrations of nitrogen oxide and the reductant.

These and other features of the present application will become apparent upon review of the following detailed description of the preferred embodiments when taken in conjunction with the drawings and the appended claims.

BRIEF DESCRIPTION OF THE DRAWINGS

These and other aspects of this invention will be more completely understood and appreciated by careful study of the following more detailed description of exemplary embodiments of the invention taken in conjunction with the accompanying drawings, in which.

DETAILED DESCRIPTION OF THE INVENTION

Reducing and controlling engine emissions of oxides of nitrogen are important considerations for internal combustion engines, particularly those used in large power generating operations. As stated, NOx emissions are an element of smog production. Stringent NOx emission limits already are mandated by state and federal governments and are likely to become even stricter in the future. One known approach to reducing NOx emissions is to reduce NOx formation by reducing combustion temperatures, such as by recirculation of exhaust gas into the engine firing chambers to dilute the combustion mixture. Even under the best of control, however, untreated engine exhaust typically contains an unacceptable level of NOx. Thus, another approach is to strip NOx from the exhaust via one or more after treatment devices.

After treatment systems are known in the art which can convert NOx to elemental $N_2$ by selective catalytic reduction in the presence of a suitable reductant, for example, ammonia ($NH_3$) in accordance with the following equations:

$$NO+NO_2+2NH_3 \rightarrow 2N_2+3H_2O$$

$$4NO+O_2+4NH_3 \rightarrow 4N_2+6H_2O$$

$$2NO_2+O_2+4NH_3 \rightarrow 3N_2+6H_2O$$

It will be recognized that specific molar match of ammonia to NOx is desired to convert all NOx (or at least a suitable portion thereof) while slipping no excess $NH_3$ into atmosphere. However, in practice, given the limitations of conventional SCR systems, this has proved to be difficult to achieve.

Figure 1:
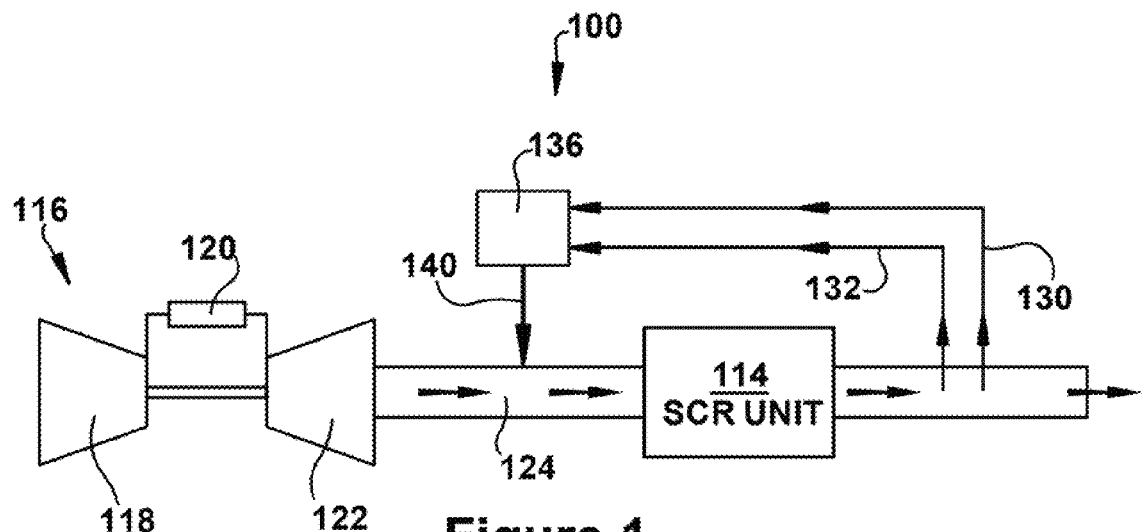
FIG. 1 is a schematic representation of a gas turbine engine and an SCR system and control configuration according to conventional design.

The present invention may be better appreciated by considering a conventional SCR system. Referring to FIG. 1, a conventional SCR system 100 comprises a selective catalytic reduction unit 114 (or "SCR unit 114") through which the combustion exhaust from an internal combustion engine 116 is directed and treated. (As shown, the internal combustion engine room is a gas turbine engine 116 that includes a compressor 118, a combustor 120 and a turbine 122, the general operation of which is known in the art.) The combustion exhaust, as shown, is directed from the gas turbine engine 116 through an upstream conduit 124 to the SCR unit 114, through which it is passed. After it passes through the SCR unit 114, the combustion exhaust continues through a downstream conduit 126 where, after passing therethrough, it may then be vented to the atmosphere, directed into a heat recovery steam generator (not shown), or used in some other manner.

The conventional SCR system 100 may further include conventional means for extracting gaseous samples from the combustion exhaust as it passes through the downstream conduit 126 and testing the samples for concentrations of NOx and a reductant. As shown, a reductant test sample 130 may be taken downstream of the SCR unit 114, and a NOx test sample 132 also may be taken downstream of the SCR unit 114. The test samples 130, 132 then may be directed to a control unit 136.

The control unit 136 may be configured to control the injection of a reductant via a reductant injector 140. The reductant injector 140 may inject reductant into the combustion exhaust at a location upstream of the SCR unit 114. It will be appreciated that the taking of the test samples, the testing of the test samples, and the injection of reductant into the combustion exhaust may be performed by conventional apparatus and systems, and the control thereof may be performed by the control unit 136 via known methods and processes. For example, in regard to the injection of reductant, an atomizing nozzle may be positioned upstream of the SCR unit 114 and may receive a regulated flow of reductant from a source and spray atomized reductant solution into the combustion exhaust. The SCR unit 114 may comprise any conventional or commercially available SCR unit that includes a catalyst disposed therein for selectively reducing NOx to $N_2$ in the presence of a reductant and $O_2$, as described above, in a known fashion.

In operation, the conventional SCR system 100 generally operates as follows. The combustion exhaust flows via the upstream conduit 124 from the gas turbine engine 116 to the SCR unit 114. The reductant injector 140 injects a flow of reductant, for example, ammonia, into the combustion exhaust as it flows through the upstream conduit 124. Within the SCR unit 114, the catalyst selectively reduces NOx into $N_2$ in the presence of the reductant and $O_2$. Downstream of the SCR unit 114, gaseous test samples 130, 132 are be taken and provided to the control unit 136, which may test the samples for concentrations of NOx and the reductant. Based upon the test results, the control unit 136 may adjust the flow of reductant through the reductant injector 140 such that NOx emissions are reduced and/or reductant slippage is reduced. For example, if the test results indicate that the level of NOx emissions is impermissibly high, the flow of reductant through the reductant injector 140 may be increased. This, in turn, should reduce an increased amount of NOx and, thereby, reduce NOx emissions. On the other hand, if the test results indicate that the level of NOx emissions is acceptable but the level of reductant emissions is impermissibly high, the flow of reductant through the productive and injector 140 may be decreased, which, in turn, should reduce the level of reductant emissions. However, as stated above, the conventional testing process includes a significant lag, which, along with other limitations, impedes the ability of the system 100 to control the process such that NOx emissions and reductant slippage are minimized or maintained at acceptable levels.

Figure 2:
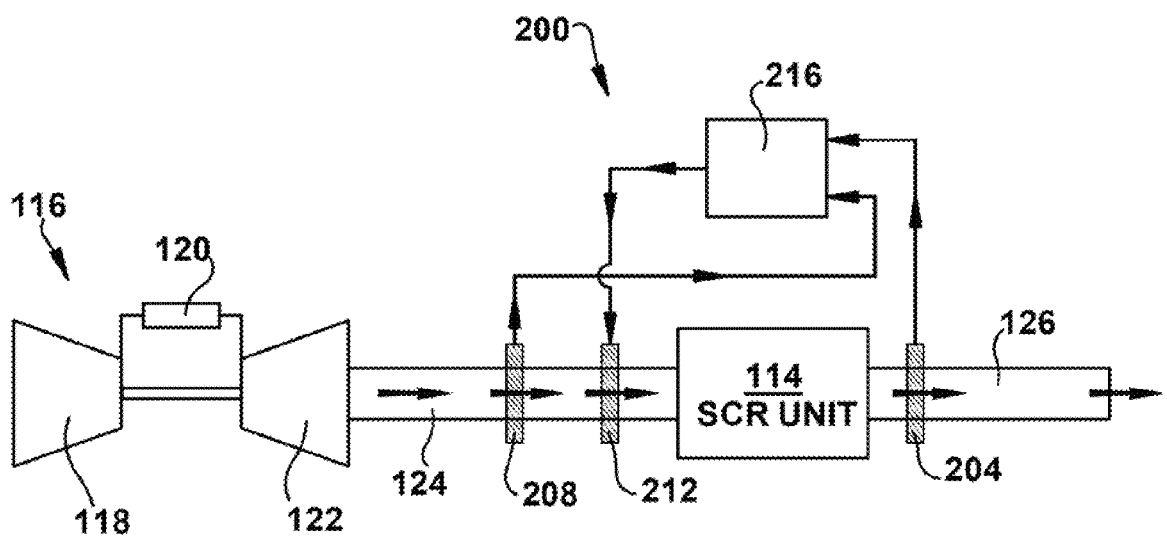
FIG. 2 is a schematic representation of a gas turbine engine and an SCR system and control configuration according to an exemplary embodiment of the present application.

Referring now to FIG. 2, an exemplary SCR system 200 in accordance with one aspect of the present application is depicted. The SCR system 200 is shown in conjunction with a gas turbine engine 100. It will be appreciated that the present invention may be used with other combustion engines and that the use of a gas turbine engine in this context is exemplary only. As shown, the SCR system 200 includes: a SCR-unit 202; a downstream tunable diode laser absorption spectroscopy unit 204 (or "downstream TDLAS unit 204"); an upstream tunable diode laser absorption spectroscopy unit 208 (or "upstream TDLAS unit 208"); a reductant injector 212; and a control unit 216. It will be appreciated that some elements of the SCR system 200 may be the same or similar to their counterparts in the conventional design described in connection with FIG. 1. For example, the SCR unit 202 may comprise a conventional SCR unit known in the art that includes a catalyst for selectively reducing NOx in the presence of a reductant, such as ammonia, and $O_2$. In some embodiments, the catalysts within the SCR unit 202 may be provided as porous or channeled monoliths, which are generally known in the art. In addition, the reductant injector 212 may be similar to the one described above. For example, atomizing nozzles may be used to spray a controlled flow of reductant into the combustion exhaust. Indeed, it will be appreciated that the present invention contemplates the introduction of a reductant (for example, ammonia) via any conventional delivery method. That is, it should be understood that all appropriate chemical reductants, including all ammoniacal chemical reductants, and all apparatus for supplying or injecting them to the exhaust flow so that they interact with the SCR catalysts are fully comprehended by the invention. However, in certain embodiments, as described in more detail below, the reductant injector 212 may take other novel configurations. Finally, it should be appreciated that, while several components are described as being part of the SCR system 200, some of the components are not necessary for certain of the claimed embodiments of the present application. For example, some embodiments of the present application may operate without the inclusion, function or control of the reductant injector 212. That is, as provided below in the claims, aspects of the present application include novel combustion exhaust monitoring capabilities that stand apart from a system that couples these monitoring capabilities with the manner in which reductant injection is controlled or manipulated.

As further anticipated by the present application, it should be understood that the downstream TDLAS unit 204 and the upstream TDLAS unit 208 may comprise conventional absorption spectroscopy technology that incorporates tunable diode lasers, the particular function of which is discussed in more detail in relation to FIGS. 3 through 8. It will be appreciated, however, that certain novel configurations and methods of operation related to how laser absorption spectrometry technology is incorporated and used in the present application also are disclosed herein, as provided below. In addition, in certain embodiments of the present application, it will be appreciated that both of the TDLAS units 204, 208 may not be present. For example, in some embodiments, the downstream TDLAS unit 204 may be present while the upstream TDLAS unit 204 is omitted in the system.

As used herein, the control unit 216 may comprise a conventional computer implemented monitoring, testing, and control device that is configured to operate as described herein. It will be appreciated that algorithms, control programs, logic flow diagrams, and/or software programs, as described in detail below, may be developed to monitor and control the operation of SCR system 200. As one of ordinary skill in the art will appreciate, the control unit 216 may include multiple sensors that monitor the relevant operational variables. These hardware devices, test equipment, and other components and systems may send data and information to and be controlled and manipulated by the control unit 216 via known methods and systems. That is, pursuant to conventional means and methods, the control unit 216 may acquire data from the other components of system 200, test samples, process/monitor the data, communicate with the operators of the system, and/or control the operation of the various devices of the system (such as the reductant injector 212 and/or the TDLAS units 204, 208) pursuant to a set of instructions or logic flow diagram, which, as one of ordinary skill in the art will appreciate, may be made part of a software program.

As discussed in more detail below, a set of instructions or flow of logic that controls the operation of the control unit 216. These instructions may be set forth in a software program, executed within the computerized control unit 216, and, generally, used to test, determined, calculate and/or monitor the properties of the combustion exhaust from the internal combustion engine 100, and/or optimize the function of a SCR system in accordance with embodiments of the present application. As one of ordinary skill in the art will appreciate, these instructions or logic may be implemented and performed by the control unit 216. In some embodiments, the control unit 216 may comprise a conventional computer. For example, but not by way of limitation, the control unit 216 may be implemented as a single special purpose integrated circuit having a main or central processor section for overall, system-level control, and separate sections dedicated performing various different specific combinations, functions and other processes under control of the central processor section. It will be appreciated by those skilled in the art that the control unit 216 also may be implemented using a variety of separate dedicated or programmable integrated or other electronic circuits or devices, such as hardwired electronic or logic circuits including discrete element circuits or programmable logic devices, such as PLDs, PALs, PLAs or the like. The control unit 216 also may be implemented using a suitably programmed general-purpose computer, such as a microprocessor or microcontrol, or other processor device, such as a CPU or MPU, either alone or in conjunction with one or more peripheral data and signal processing devices. In general, any device or similar devices on which a finite state machine capable of implementing the instructions/logic flow and the other functions described herein may function capably as the control unit 216.

Figure 3:
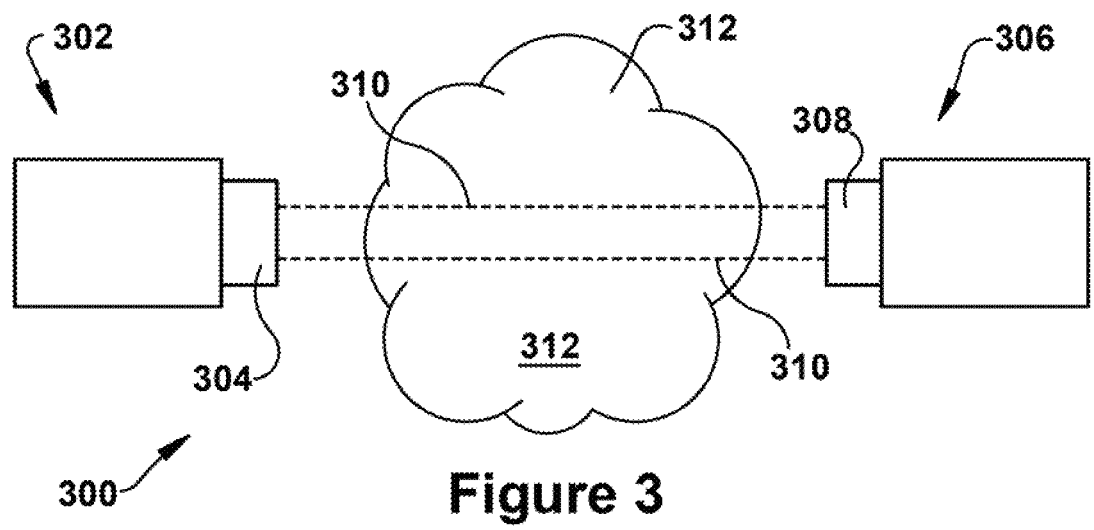
FIG. 3 is a schematic representation of the principles of tunable diode laser absorption spectroscopy as may be used in accordance with embodiments of the present application.

As stated, the downstream TDLAS unit 204 and the upstream TDLAS unit 208 may comprise any conventional absorption spectroscopy technology that incorporates tunable diode lasers. (In other embodiments, other types of tunable and non-tunable lasers may be used. Tunable diode lasers are used in the description as a preferred and highly functional alternative for this type of absorption spectroscopy application.) FIG. 3 is a schematic representation of the principles of tunable diode laser absorption spectroscopy as may be used in accordance with embodiments of the present application. As shown, this simplified illustration shows a tunable diode laser absorption spectroscopy unit 300 generally that includes a laser emitter 302, which may include emitter optics 304, and a laser detector or receiver 306, which may include receiver optics 308. Tunable diode laser absorption spectrometry generally creates one or more lasers that are directed along laser paths 310 (i.e., the dotted lines). The lasers are emitted by the laser emitter 302 such that they travel through an absorbing medium 312 (i.e., the medium that is being tested for specie concentrations). After passing through the absorbing medium, the laser is received by the laser receiver 306. This technique accesses the concentration or amount of a species in the absorbing medium 312 by relating the level of specie concentration to the absorption of the laser by the absorbing medium 312. In general, laser-based optical spectroscopic techniques have great potential for the detection and monitoring of constituents in a gaseous medium. The technique generally provides a number of important advantages, e.g. a high sensitivity and a high selectivity with non-intrusive and remote sensing capabilities.

In some embodiments, the laser emitter 302 may comprise a tunable laser. In general, a tunable laser is one whose wavelength of operation can be altered in a controlled manner. This feature allows flexibility of use and is a reason as to why tunable lasers are describe herein in conjunction with preferred embodiments. As one of ordinary skill in the art will appreciate, there are many types and categories of tunable lasers. They exist in the gas, liquid, and solid state. Among the types of tunable lasers are excimer lasers, CO2 lasers, dye lasers (liquid and solid state), transition metal solid-state lasers, semiconductor diode lasers, and free electron lasers. All of these are possible alternatives contemplated by the present application, with tunable diode lasers being a particularly preferred embodiment. As part of a TDLAS application, tunable diode lasers are designed to focus on single absorption wavelengths specific to a compound of concern (i.e., a specie) in the gaseous form. Tunable diode lasers are capable of achieving low detection limits and are virtually interferent-free. As will be appreciated by one of ordinary skill in the relevant art, quantitative measurements in direct gas phase laser absorption spectroscopy are often based on Beer's Law, which states that for a constant path length the intensity of the incident light energy traversing an absorbing medium diminishes exponentially with concentration.

More specifically, the Beer-Lambert law describes the relationship between incident and transmitted spectral intensities when the laser beam passes through an uniform gaseous medium. When spectrally narrow radiation at frequency v passes through an uniform gaseous medium of length L [cm], the transmitted intensity $I_t$ is related to the incident intensity $I_0$ as:

$$\left(\frac{I_t}{I_0}\right)_v = \exp(-k_v L)$$

where $k_v$ [cm$^{-1}$] is the spectral absorption coefficient. For an isolated transition i (for a laer), $$k_v = P x_{abs} S_i(T) \phi_v$$

where P[atm] is the total pressure of the gas, $x_{abs}$ is the mole fraction of the absorption species of interest $S_i(T)$[cm$^{-2}$ atm$^{-1}$] is the line strength of the transition at temperature T[K], and $\phi_v$ [cm] is the line shape function. The line shape function $\phi_v$ is normalized such that:

$$\int_{-\infty}^{\infty} \phi_v \, dv \equiv 1$$

The species concentration (mole fraction) can then be determined as:

$$x_{abs} = \frac{\ln\left(\frac{I_0}{I_t}\right)_v}{P S_i(T) L}$$

The above equation indicates that the molecular density is a function of reference and transmitted intensity of the laser.

In general, a tunable diode laser instrument, i.e., the laser emitter 302, according to the present invention includes a diode to generate light within a narrow frequency range that contains a relatively unique absorption wavelength of the chemical of interest. The laser frequency may be "tuned" by changing the temperature of the diode or by changing the current being fed to it or both. In this manner, the wavelength of the laser may be made to match the spectral absorption line of interest. The degree of absorption at a specific locked on wavelength can be used to calculate a concentration, or it can be calculated using a small wavelength range about the absorption line of interest that is built up in a signal averager and the concentration is calculated from this. Multiple chemicals can be monitored by multiplexing the instrument with more than one diode. Detection limits are dependent upon the pressure and temperature of the gas and the path length, among other things, with shorter path lengths producing higher detection limits. Commercially available diodes generally are semiconductors, fabricated from exact combinations of ultra pure materials. The basic materials of construction of these diodes include gallium (Ga), indium (In), arsenic (As), antimony (Sb), phosphorus (P), aluminum (Al), lead (Pb), tin (Sn), selenium (Se), tellurium (Te), and sulfur (S).

The laser receiver 306 of the present application may include any conventional laser detector, including photodiodes. Photodiodes can be constructed from a variety of materials. Optics 304, 308 may be included to focus the laser path as needed.

In use, as generally shown in FIG. 3, the tunable diode laser absorption spectroscopy unit 300 may operate as follows. The laser emitter 302 may emit a laser at wavelength that coincides with the absorption wavelength of a compound of interest, such as NOx, NH$_3$ or water vapor, that is contained within the absorbing medium 312, which, in the present application comprises the combustion exhaust of an engine. The laser receiver 306 may be positioned such that it receives the emitted laser after the laser passes through the absorbing medium 312. Pursuant to known methods, the concentration of the specie or compound of interest within the absorbing medium 312 may be calculated based upon the level of absorption experienced by the laser as it passed through the absorbing medium 312, which may be calculated based upon laser detected by the laser receiver 306.

Figure 4:
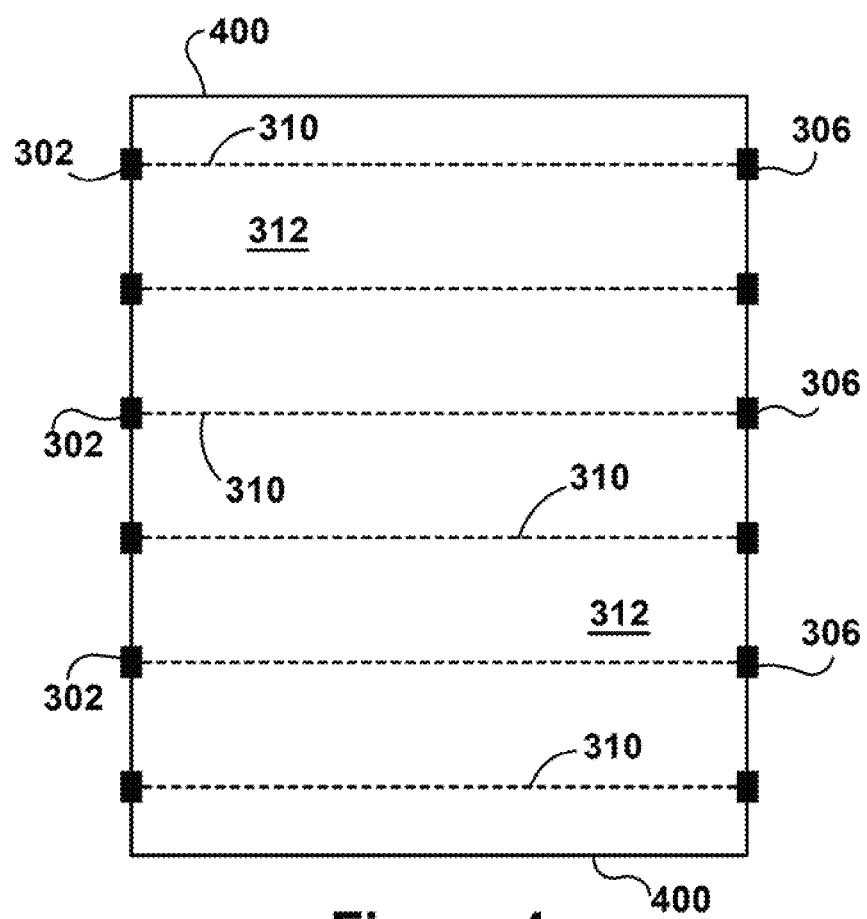
FIG. 4 is a schematic representation of a laser transmitter/receiver configuration according to an exemplary embodiment of the present application.

FIG. 4 is a schematic representation of a laser transmitter/receiver configuration according to an exemplary embodiment of the present application. As will be appreciated, FIG. 4 represents a cross-section of a conduit 400 through which an absorbing medium 312 passes. Relating to the exemplary embodiment of the present application, the conduit 400 may represent the upstream conduit 124, the downstream conduit 126, or both. Within the conduit 400, ports may be installed opposite each other. On one side of the conduit 400, the ports may comprise laser emitters 302. Opposite the laser emitters 302, the ports may comprise laser receivers 306. Pursuant to known methods, lasers may be emitted from the laser emitters 302 and oriented such that the lasers traverse laser paths 310 (and travel through the absorbing medium 312). The wavelength of the lasers may be predetermined such that it matches the absorption wavelength of a gaseous specie or specie of interest within the absorbing medium 312. In this manner, the concentration of the specie may be determined based upon the absorption of the laser as it travels across the absorbing medium 312. After passing through the absorbing medium 312, the lasers are then received by the laser receivers 306. The laser receiver 306 detects the level of absorption by comparing the laser that is received to the laser that was emitted. Based upon the level of absorption, a concentration of a gaseous species within the absorbing medium 312 then may be calculated.

Given the horizontal alignment of the laser paths 310 in FIG. 4, data relating to the spatial distribution of specie concentrations is fairly limited. That is, spatial distribution is generally confined to the concentrations measured at each horizontal level between each laser emitter 302/laser receiver 306 pairing. Thus, given the laser path 310 orientation of FIG. 4, an average concentration of the specie of interest may be determined at each level (i.e., between each emitter 302/receiver 306 pairing) and the different levels may be compared, but further detail regarding the spatial distribution of specie concentrations is not feasibly attainable.

Figure 5:
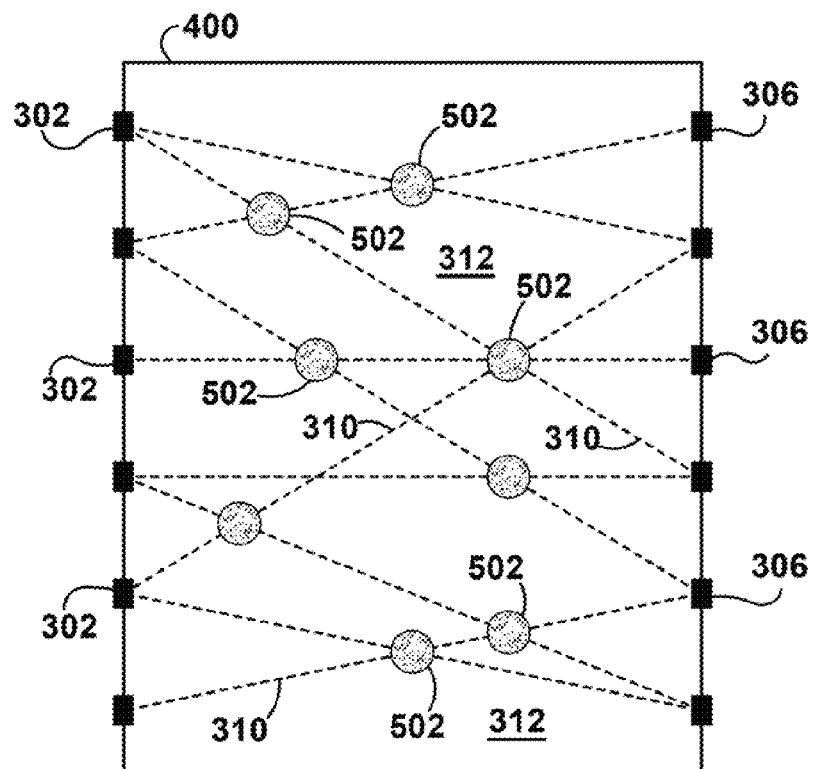
FIG. 5 is a schematic representation of a laser transmitter/receiver configuration according to an exemplary embodiment of the present application.

FIG. 5 illustrates an alternative configuration of laser paths 310 according to an exemplary embodiment of the present invention. As shown, in this case, laser emitters 302 may be oriented such that multiple, intersecting laser paths are created. Thus, for example, a laser emitter 302 may be trained on the laser receiver 306 that is directly across from it and/or on a second for a third laser receiver 306 that is positioned in a different row (thereby creating one or more intersecting, diagonal laser paths 310).

Also represented in FIG. 5 are several "data clouds" 502. The data clouds 502 are visual representations regarding the spatial distribution of specie concentrations that may be gleaned from the acquired data given the intersecting laser paths 310. As shown in FIG. 5, spatial distribution information of specie concentrations includes two categories of data: 1) the data associated with the average concentration measured between each emitter 302/receiver 306 paring; and 2) that calculations of probable specie concentrations or probable concentrations that may be made at each of the intersecting laser paths 310 (which may be approximated based upon the average concentrations measured along each of the intersecting pathways 310). In this manner, as illustrated by the several data clouds 502, improved data relating to spatial distribution of specie concentration may be calculated. That is, the many intersections of the laser paths 310 provide indications as to the specie concentrations at a grid-like cross-section of the conduit 400.

Figure 6:
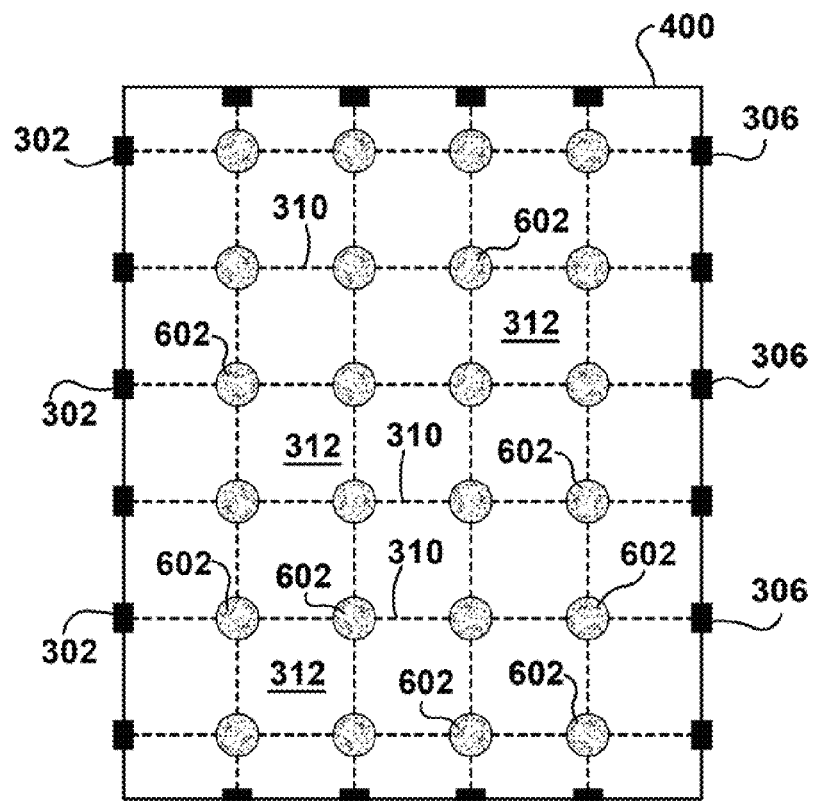
FIG. 6 is a schematic representation of a laser transmitter/receiver configuration according to an exemplary embodiment of the present application.

FIG. 6 illustrates another alternative configuration of laser paths 310 according to an exemplary embodiment of the present invention. In this case, laser emitters 302 may be located on two sides of the rectangular conduit 400 and, opposite the laser emitters 302, laser receivers 306 may be located on the other two sides of the rectangular conduit 400. In this manner, as illustrated by the several data clouds 602, improved data relating to spatial distribution of specie concentration may be calculated in the same way discussed above in relation to FIG. 5. Of course, the laser path 310 configurations provided are exemplary and others are possible. One of ordinary skill in the art will appreciate that other configurations using combinations of those shown in FIGS. 5 and 6 as well as configurations using more or less laser emitters 302/laser receivers 306 are possible, and are fully contemplated by the present application.

It will be appreciated that the upstream TDLAS unit 208 and/or the downstream TDLAS unit 204 may include TDLAS units configured as those shown in FIG. 4, 5, or 6, or other configurations. In addition, as stated, each of the laser paths 310 indicated may include lasers of multiple wavelengths which are designed to measure the concentrations of multiple gaseous species simultaneously. In one preferred application, the absorbing medium 312 may be the combustion exhaust of a combustion engine and the gaseous species concentrations measured by the TDLAS units 204, 208 may include a reductant (such as ammonia), NOx, and/or water vapor. (As discussed in more detail below, it will be appreciated by those skilled in the art that the broad absorption spectra for water vapor may be used to accurately measure the temperature of the combustion exhaust as well as to correct for an interference water vapor may have caused as the wave lengths used for the reductant or NOx.)

Figure 7:
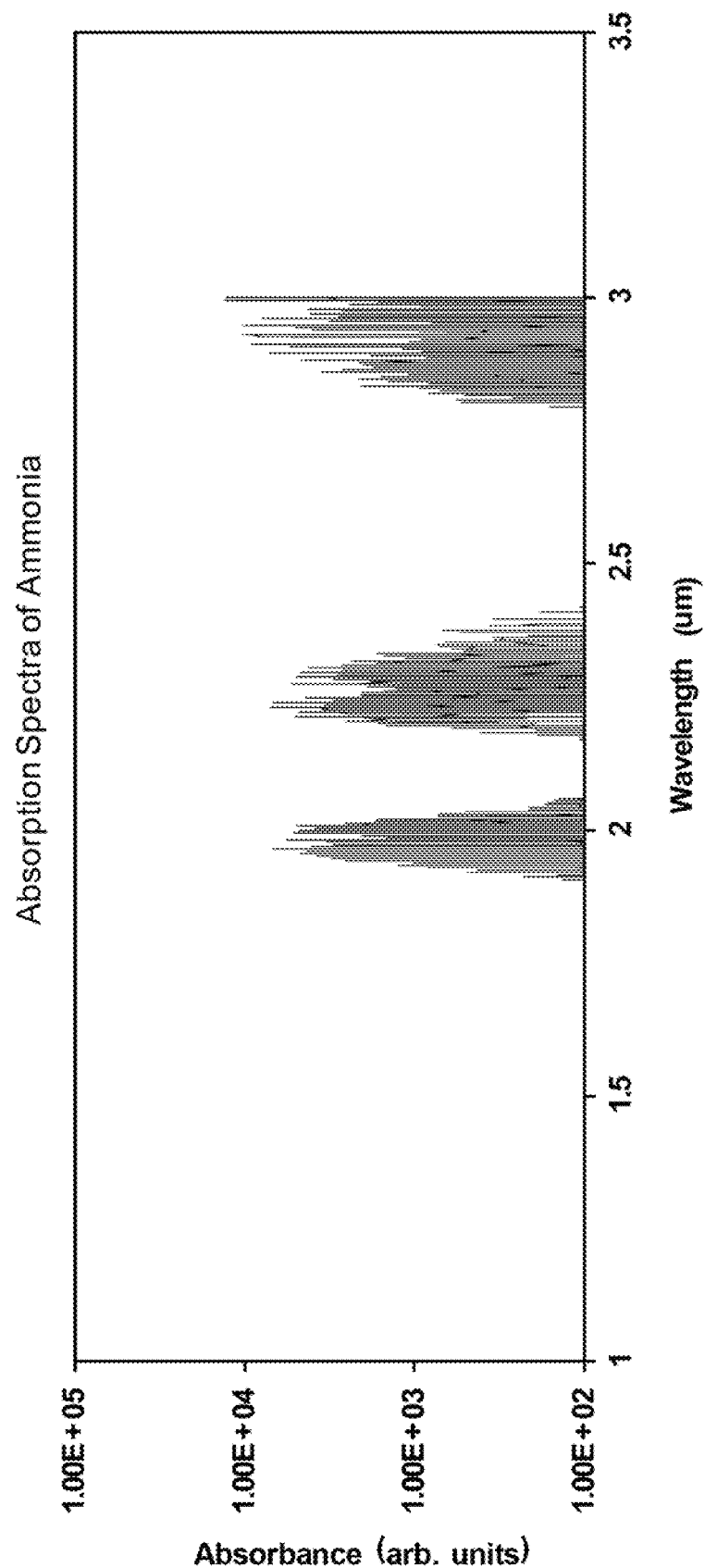
FIG. 7 is a graph illustrating experimental data relating to the absorption spectra of ammonia.

FIG. 7 is a graph illustrating experimental data developed by the inventors of the present application relating to the absorption spectra of ammonia at relevant temperatures, which may be used to effectively tune the wavelength for the laser diode used in the present invention for the purposes of measuring the concentration of ammonia. As shown, it has been discovered that an effective absorption spectra for ammonia may comprise wavelengths of between approximately 1.5 and 3.5 μm. Given the adsorption spectra of other constituents within the combustion exhaust (which may cause interference with the ammonia concentration measurement) and the experimental results shown in FIG. 7, in a more preferred embodiment, an ammonia absorption spectra of between approximately 1.9 and 2.1 μm may be used. In another more preferred embodiment, an ammonia absorption spectra of between approximately 2.2 and 2.4 μm may be used.

Figure 8:
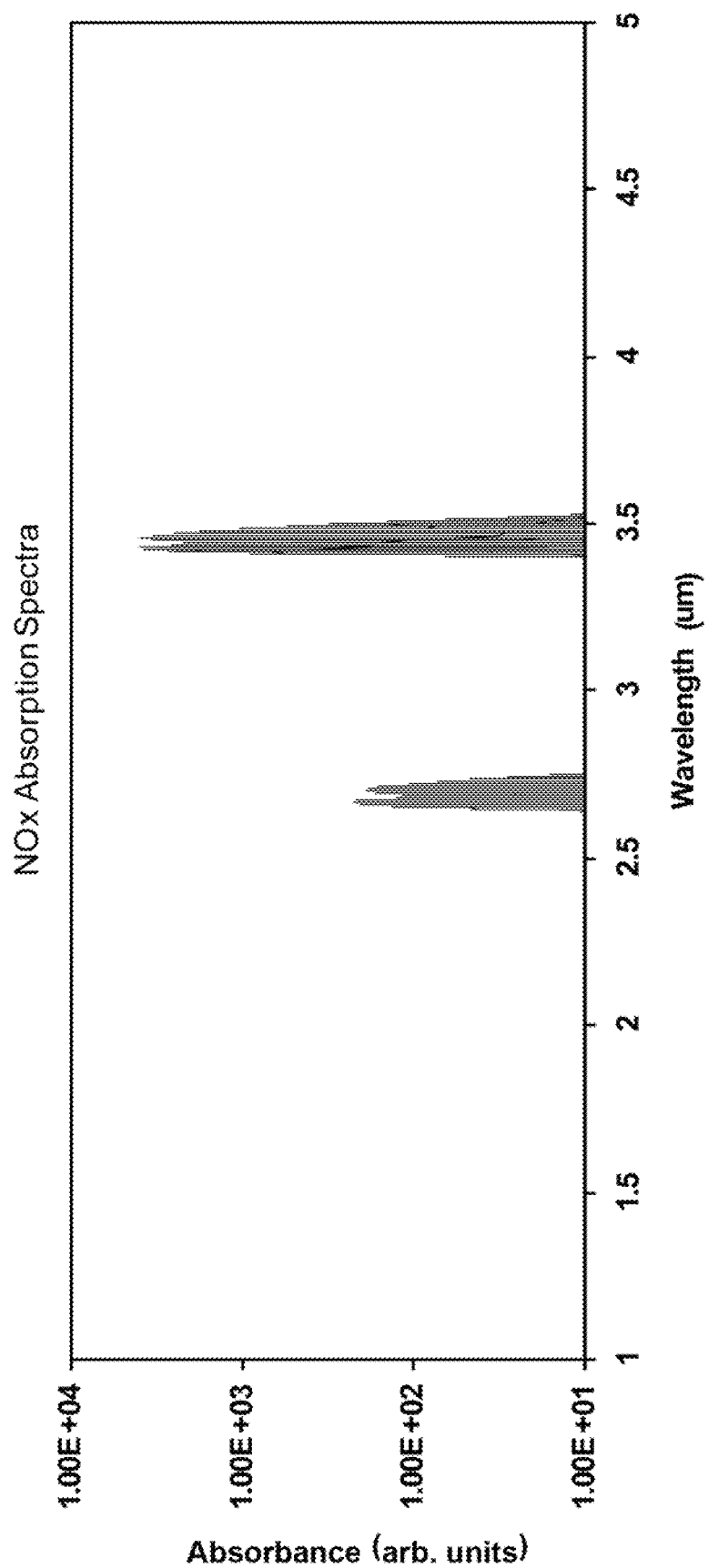
FIG. 8 is a graph illustrating experimental data relating to the absorption spectra of NOx.

FIG. 8 is a graph illustrating experimental data developed by the inventors of the present application relating to the absorption spectra of NOx at relevant temperatures, which may be used to effectively tune the wavelength for the laser diode used in the present invention for the purposes of measuring the concentration of NOx. As shown, it has been discovered that an effective absorption spectra for NOx may comprise wavelengths of between approximately 2.5 and 4.0 μm. Given the adsorption spectra of other constituents within the combustion exhaust (which may cause interference with the NOx concentration measurement) and the results shown in FIG. 8, in one more preferred embodiment, a NOx absorption spectra of between approximately 2.6 and 2.8 μm may be used. In another more preferred embodiment, a NOx absorption spectra of between approximately 3.4 and 3.6 μm may be used.

Figure 9:
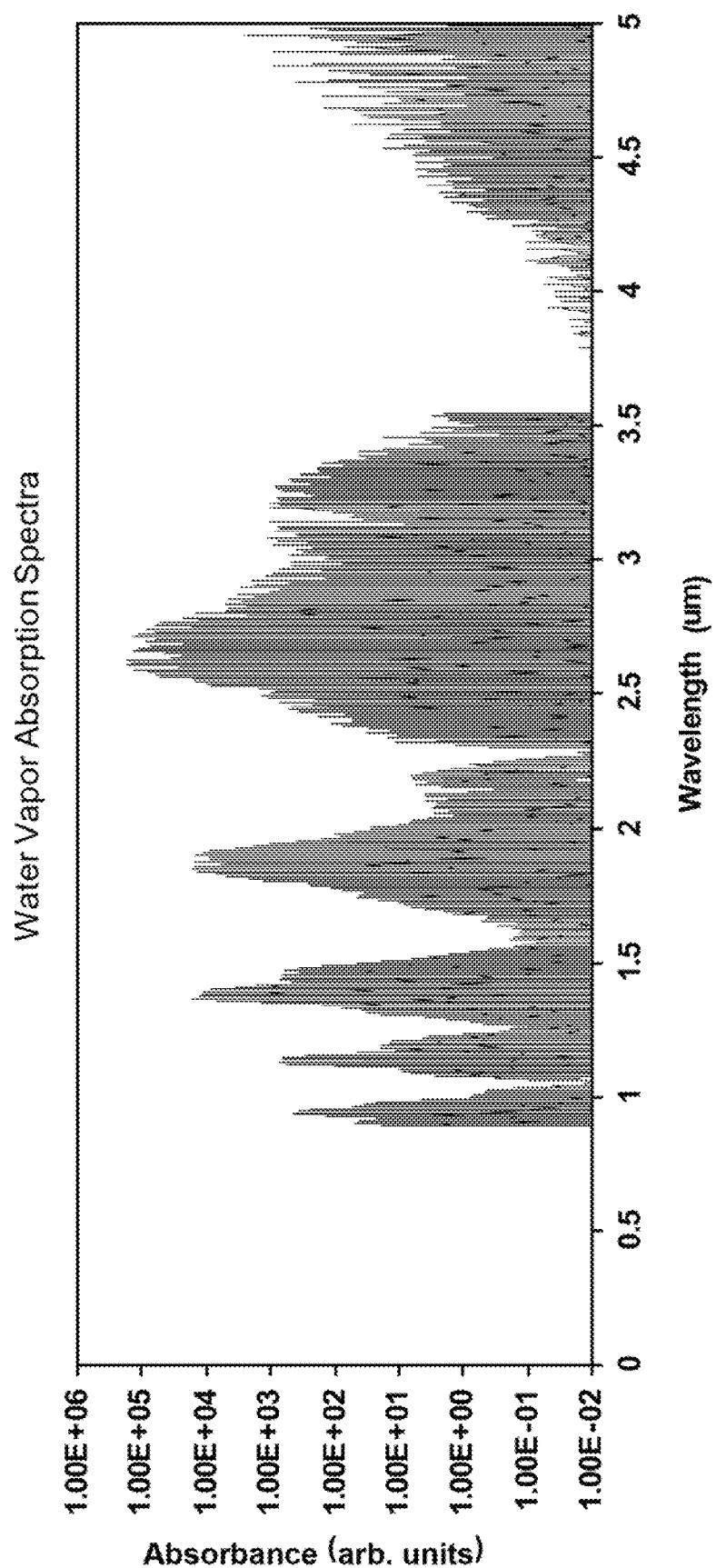
FIG. 9 is a graph illustrating experimental data relating to the absorption spectra of water vapor.

FIG. 9 is a graph illustrating experimental data developed by the inventors of the present application relating to the absorption spectra of water vapor at relevant temperatures, which may be used to determine the temperature of the exhaust flow. As one of ordinary skill in the art will appreciate, temperature can be inferred from the measured ratio of peak absorbance for two different temperature-dependent transitions. The ratio of two peak absorbances is given by:

$$R = \frac{P_{abs}L\phi_{v1}S_1(T)}{P_{abs}L\phi_{v2}S_2(T)} = \frac{S_1(T)\phi_{v1}}{S_2(T)\phi_{v2}}$$

where $\phi_v$ [cm] is the line shape function of a particular laser transition. The line shape function $\phi_v$ is normalized such that $$\int_{-\infty}^{\infty} \phi_v \, dv \equiv 1.$$

Then the ratio becomes:

$$R = \frac{S_1(T)}{S_2(T)}$$

In this manner, the temperature of the exhaust flow may be determined by present embodiments of the present invention.

In addition, because of the water vapor has a wide absorption band in the infrared range, the presence of water vapor in the exhaust flow generally results in a cross-absorption of the sensing laser due to the combination of water molecules and ammonia or NOx being present in the flow. That is, the water vapor will cause the NOx and/or ammonia sensing lasers to show levels that are higher than actual specie content in the absorption medium. To mitigate this error of cross-absorption, a laser at a wavelength that does not absorb NOx or ammonia may be used so that water vapor may be subtracted from levels of NOx or ammonia measured at the other wavelengths. Using the equation, the concentration of water present in the gas may be estimated:

$$x_{Water} = \frac{\ln\left(\frac{I_0}{I_{Water}}\right)_v}{PS_i(T)L}$$

In the case of ammonia, the equation becomes:

$$x_{NH3+Water} = \frac{\ln\left(\frac{I_0}{I_{NH3+Water}}\right)_v}{PS_i(T)L}$$

Hence, it will be appreciated that, the corrected concentration of ammonia present in the exhaust gas would be:

$$x_{NH3} = x_{NH3+Water} - x_{Water}$$

As shown in FIG. 9 (and taking into account the absorption wavelengths of ammonia and NOx), it has been discovered that an effective absorption spectra for water vapor may comprise wavelengths of between approximately 0.9 and 1.5 μm. In a more preferred embodiment, a water vapor absorption spectra of between approximately 1.1 and 1.3 μm may be used.

In operation, pursuant to the systems, components, and methodologies described above, the SCR system 200 may operate as follows. The combustion exhaust may flow from a combustion engine (in this case, gas turbine engine 116) via the upstream conduit 124 to the SCR unit 114. The upstream TDLAS unit 208, which may be positioned just upstream of the SCR unit 114, may measure the temperature of and/or the concentration of NOx within the flow of combustion exhaust. The upstream TDLAS unit 208 may provide the data relating to the measure temperature and concentration of NOx to the control unit 216, as shown. In accordance with the present application, this data may be available in a very short amount of time from the measurement, for example, in less than a second.

Downstream of the upstream TDLAS unit 208, the reductant injector 212 may inject a flow of reductant, for example, ammonia, into the combustion exhaust as it flows through the upstream conduit 124. Within the SCR unit 114, the catalyst may selectively reduce NOx to $N_2$ in the presence of the reductant and $O_2$.

Downstream of the SCR unit 114, in the downstream conduit 126, the downstream TDLAS unit 204 may measure the temperature of, the concentration of NOx within, and/or the concentration of reductant within the flow of combustion exhaust exiting the SCR unit 114. The downstream TDLAS unit 204 may provide the data relating to the measured temperature and concentrations of NOx and reductant to the control unit 216, as shown. Again, this data may be provided in a very short period of time after the taking of the measurement, for example, in less than 1 second.

As stated, given the arrangement, configuration, and components of system 200, the TDLAS units 204, 208 provide the data relating to the measurement of the temperature of and/or concentrations of the relevant species within the exhaust after the passage of a relatively short period of time. In this manner, substantially current data relating to the temperature and concentrations of reductant and/or NOx may be monitored. As discussed, the TDLAS may correct for cross-absorption of water vapor at wavelengths intended to measure other specie concentrations by measuring the concentrations of water vapor at a wave length that does not absorb the other relevant gaseous species.

In some embodiments of the present invention, based upon the current temperature and/or concentration data, the control unit 216 may adjust the flow of reductant through the reductant injector 212 pursuant to a control algorithm such that NOx emissions are closely maintained at or below a predetermined target level and/or reductant slippage is maintained at or below a predetermined or target level. For example, if the test results indicate that the level of NOx emissions is above a predetermined target level, the flow of reductant, for example, ammonia, through the reductant injector 140 may be increased by the control unit 216. This, in turn, allows an increased amount of NOx to be reduced within the SCR unit 114, thereby, reducing NOx emissions. In this case, timely data (i.e., less than about a 1 second lag, or, in some case, less than 0.1 second lag) reflecting substantially current NOx and ammonia concentrations and exhaust temperatures may be measured periodically and provided to the control unit 216 such that the control unit 216 may continue to adjust the reductant injection rate pursuant to the control algorithm. In this manner, the NOx emissions may be reduced and the injection rate of ammonia maintained at a level that does not result in significant reductant slippage. On the other hand, if the test results indicate that the level of NOx emissions is acceptable but the level of ammonia emissions (or slippage) is impermissibly high, the flow of ammonia through the reductant injector 140 may be decreased by the control unit 216. This, in turn, decreases the amount of NOx reduced within the SCR unit 114, which will result in increased levels of NOx emissions. However, the ammonia slippage should be reduced. As before, timely data (i.e., less than about a 1 second lag, or, in some case, less than 0.1 seconds lag) reflecting substantially current NOx and ammonia concentrations and exhaust temperatures may be provided to the control unit 216 such that the control unit 216 may continue to adjust the reductant injection rate pursuant to the control algorithm, thereby maintaining acceptable NOx and ammonia emission levels.

In at least certain applications, the present invention affords several advantages.

First, the system according to the present invention provides accurate and timely measurement data so that the selective catalytic reduction processes may be monitored closely and/or controlled in a manner such that NOx and reductant emissions are reduced or minimized. As described, the system of the present invention provides measurement data with a lag time of less than a second so that the current conditions of the selective catalytic reduction process may be known and monitored. With this type of timely data, it will be appreciated that the quickly changing conditions associated with transient operating periods (i.e., start-up, load swings, etc.) may be known and reacted to in a timely manner. The ability to do this may allow reductant injection rates to be adjusted based on current conditions, which will reduce reductant slippage and NOx emissions.

Second, while conventional systems generally lack accurate temperature data in the specie concentration measurement location, the system in accordance with the present invention provides accurate temperature data at the same location where specie concentration data is collected. Because ammonia absorption rates are dependent on temperature, accurate data of this nature is necessary to control of the process in a manner that reduces or minimizes the emission of excess NOx and/or ammonia.

Third, while conventional systems generally lack information regarding the spatial distribution of the relevant compounds through the exhaust, the system of the present invention, as described above, may be configured such that data of nature may be obtained in a timely and cost-effective manner, and in a manner that does not interfere with the flow of combustion exhaust through the conduit. Conventional extractive technologies would require lengths of conduit to extend into the flowpath of the exhaust, which would be cumbersome, costly to construct and maintain, and potentially affect the flow of the exhaust.

Fourth, while conventional systems generally only measure exhaust composition downstream of SCR, the present system allows the upstream measurement of exhaust gases and provides measurement results in a timely manner so that the upstream measurement may be meaningful (i.e., effectively used in a control algorithm to enhance the operation of the SCR system). More particularly, the measurement lag time associated with conventional systems generally meant that gaseous composition measurements upstream of the SCR unit were not useful (or not as useful as they could be). As a result, conventional systems focused on measurements downstream of the SCR unit. Of course, at this location, no matter what the downstream measurements indicated, any gas there was beyond the SCR unit (i.e., treatment) and would be released into the atmosphere. In the present system, measurement results can be provided virtually instantaneously (as stated, in less than 1 second, and, in some applications, less than 0.1 seconds) and, being made upstream of the reductant injector 212 and the SCR unit 114, provides the opportunity to adjusted treatment variables (for example, the amount of reductant injected into the exhaust flow by the reductant injector may be increased) so that the exhaust gas being measured may also be treated before being released into the atmosphere.

Fifth, spatial concentration data provides the opportunity to inject the reductant into the exhaust flow in a manner such that concentrated areas of NOx may be treated with an increased concentration of reductant. The similar distribution of NOx and reductant (i.e., areas of high concentration of NOx coincides with areas of high concentration of ammonia and areas of low concentration of NOx coincides with areas of low concentration of ammonia) provides for more efficient reduction of NOx within the SCR unit, lower levels of NOx emission, and lower levels of reductant slippage. Several types of reductant injection systems may be used to provide for a controlled distribution of reductant in this manner. One such system may include several reductant injectors that project into the flow path of the exhaust and provide several injection nozzles that are spaced evenly over the cross-sectional area of the conduit. Another such system may include several reductant injection nozzles that are spaced around the periphery of the conduit. Another such system may include a combination of reductant injection nozzles that project into the flowpath and those that are positioned along the periphery.

In addition, some of the injection nozzles (either those along the periphery or those that project into the flowpath) may be made such that the direction in which their spray is aimed may be controlled. It will be appreciated that the flow of reductant to the several nozzles may be varied such that reductant is applied through the cross-section unevenly so that it addresses the uneven distribution of NOx in a desired manner. In other embodiments, if concentrated areas of NOx or ammonia develop or uneven temperature distributions arise, the flow patterns through the conduit may be modified so that more mixing and greater continuity is achieved. This may be achieved through the usage of adjustable airfoils or surfaces that may be projected into the exhaust flow and maneuvered until a desired level of consistency through the exhaust flow is achieved. The control feedback loop that may be provided via that concentration measurements and the spatial distribution of the various specie gases calculated by the several embodiments of the present application may be used to achieve this aim.

As one of ordinary skill in the art will appreciate, the many varying features and configurations described above in relation to the several exemplary embodiments may be further selectively applied to form the other possible embodiments of the present invention. For the sake of brevity and taking into account the abilities of one of ordinary skill in the art, all of the possible iterations is not provided or discussed in detail, though all combinations and possible embodiments embraced by the several claims below or otherwise are intended to be part of the instant application. In addition, from the above description of several exemplary embodiments of the invention, those skilled in the art will perceive improvements, changes and modifications. Such improvements, changes and modifications within the skill of the art are also intended to be covered by the appended claims. Further, it should be apparent that the foregoing relates only to the described embodiments of the present application and that numerous changes and modifications may be made herein without departing from the spirit and scope of the application as defined by the following claims and the equivalents thereof.

We claim:

1. A system for the monitoring and/or controlling emission levels of nitrogen oxide and a reductant from a stream of combustion exhaust from an internal combustion engine, wherein the internal combustion engine includes a selective catalytic reduction unit disposed in the stream of combustion exhaust between an upstream conduit that directs the stream of combustion exhaust to the selective catalytic reduction unit and a downstream conduit that directs the stream of combustion exhaust away from the selective catalytic reduction unit, the selective catalytic reduction unit having a catalyst that is configured to catalytically reduce nitrogen oxides contained in the combustion exhaust to elemental nitrogen in the presence of a reductant and oxygen, and wherein the internal combustion engine further includes a reductant injector that injects the reductant into the flow of combustion exhaust upstream of the selective catalytic reduction unit, the system comprising:

a laser absorption spectroscopy unit that is disposed in the downstream conduit and configured to measure the concentration levels of at least nitrogen oxide and the reductant in the stream of combustion exhaust; and a control unit;

wherein the laser absorption spectroscopy unit is configured to provide timely data to the control unit relating to the measured concentration levels of nitrogen oxide and the reductant.

2. The system in accordance with claim 1, wherein timely data comprises data that comprises a lag time of less than 1 second.

3. The system in accordance with claim 1, wherein timely data comprises data that comprises a lag time of less than 0.1 seconds.

4. The system in accordance with claim 1, wherein the laser absorption spectroscopy unit comprises a tunable diode laser; and wherein the reductant comprises ammonia.

5. The system in accordance with claim 4, wherein:
the laser absorption spectroscopy unit comprises a first tunable diode laser spectroscopy unit;
the system further comprises a second tunable diode laser spectroscopy unit that is disposed upstream of the reductant injector in the upstream conduit; and
the second tunable laser absorption spectroscopy unit is configured to measure the concentration level of at least nitrogen oxide in the stream of combustion exhaust and provide timely data to the control unit relating to the measured concentration level of nitrogen oxide.

6. The system in accordance with claim 5, wherein:
the downstream conduit comprises a cross-sectional shape that includes a first side that opposes a second side across the interior of the downstream conduit;
the first side and the second side each comprises a series of ports that are arranged such that a plurality of ports on the first side opposes a plurality of ports on the second side;
the first tunable diode laser spectroscopy unit includes a plurality of laser emitters and a plurality of laser receivers that are disposed in the ports such that the laser emitters generally oppose the laser receivers across the interior of the downstream conduit; and
the laser emitters are configured to emit lasers at predetermined wavelengths that traverse predetermined laser paths and are received by at least one of the laser receivers.

7. The system in accordance with claim 6, wherein each of the laser emitters is paired with one of the laser receivers and each pair directly opposes each other across the interior of the downstream conduit; and
wherein the control unit is configured to calculate spatial distribution data relating to the spatial distribution of the measured concentration levels of nitrogen oxide and ammonia, the spatial distribution data reflecting the variation of nitrogen oxide and ammonia concentration levels measured along the laser paths.

8. The system in accordance with claim 6, wherein:
the positioning and orientation of the laser emitters and the laser receivers are configured such that a plurality of intersecting laser paths is created; and
the laser paths include at least a) laser paths that extend from the laser emitter directly across the interior of the downstream conduit to the laser receiver that directly opposes it, and b) laser paths that extend diagonally from the laser emitter across the interior of the downstream conduit to one of the laser receivers that does not directly oppose it.

9. The system in accordance with claim 8, wherein the positioning and orientation of the laser emitters and the laser receivers are configured such that the locations of the laser path intersections form an approximate grid across a cross-sectional area of the downstream conduit.

10. The system in accordance with claim 8, wherein the control unit is configured to calculate spatial distribution data relating to the spatial distribution of the concentration levels of nitrogen oxide and ammonia, the spatial distribution data reflecting: a) the variation between nitrogen oxide and ammonia concentration levels measured along each of the several laser paths; and b) the variation between probable nitrogen oxide and ammonia concentration levels that are calculated at the laser path intersections, wherein the probable nitrogen oxide and ammonia concentration levels are based upon the measured concentration levels of nitrogen oxide and ammonia along each of the laser paths that intersect to form the laser path intersections.

11. The system in accordance with claim 6, wherein:
the cross-sectional shape of the downstream conduit further comprises a third side that opposes a fourth side across the interior of the downstream conduit;
the third side and the fourth side each comprises a series of ports that are arranged such that a plurality of ports on the third side opposes a plurality of ports on the fourth side;
the first tunable diode laser spectroscopy unit further includes a plurality of laser emitters and a plurality of laser receivers that are disposed in the ports of the third and fourth side of the downstream conduit such that the laser emitters generally oppose the laser receivers across the interior of the downstream conduit;
the laser emitters disposed along the third and fourth side of the downstream conduit are configured to emit lasers at predetermined wavelengths that traverse predetermined laser paths and are received by at least one of the laser receivers disposed along the third and fourth side of the downstream conduit;
the positioning and orientation of the laser emitters and the laser receivers disposed on the first side, second side, third side, and fourth side are configured such that a plurality of intersecting laser paths is created that include laser paths extending from the first side to the second side intersecting laser paths that extend from the third side to the fourth side;
the control unit is configured to calculate spatial distribution data relating to the spatial distribution of the concentration levels of nitrogen oxide and ammonia, the spatial distribution data reflecting: a) the variation between nitrogen oxide and ammonia concentration levels measured along each of the several laser paths; and b) the variation between probable nitrogen oxide and ammonia concentration levels that are calculated at the laser path intersections, wherein the probable nitrogen oxide and ammonia concentration levels are based upon the measured concentration levels of nitrogen oxide and ammonia along each of the laser paths that intersect to form the laser path intersections.

12. The system in accordance with claim 6, wherein the predetermined wavelengths comprise at least an absorption wavelength relating to nitrogen oxide and an absorption wavelength relating to ammonia.

13. The system in accordance with claim 12, wherein:
the absorption wavelength relating to nitrogen oxide comprises a range of between approximately 2.5 and 4.0 µm; and
the absorption wavelength relating to ammonia comprises a range of between approximately 1.5 and 3.5 µm.

14. The system in accordance with claim 12, wherein:
the absorption wavelength relating to nitrogen oxide comprises a range of between approximately 2.6 and 2.8 µm; and
the absorption wavelength relating to ammonia comprises a range of between approximately 1.9 and 2.1 µm.

15. The system in accordance with claim 12, wherein:
the absorption wavelength relating to nitrogen oxide comprises a range of between approximately 3.4 and 3.6 µm; and
the absorption wavelength relating to ammonia comprises a range of between approximately 2.2 and 2.4 µm.

16. The system in accordance with claim 12, wherein:
the predetermined wavelengths comprise at least an absorption wavelength relating to water vapor; and
the absorption wavelength relating to water vapor comprises a range of between approximately 0.9 and 1.5 µm.

17. The system in accordance with claim 13, wherein:
the predetermined wavelengths comprise at least an absorption wavelength relating to water vapor; and
the absorption wavelength relating to water vapor comprises a range of between approximately 1.1 and 1.3 µm.

18. The system in accordance with claim 16, wherein the laser absorption spectroscopy unit is configured to measure a temperature of the stream of combustion exhaust based upon water vapor absorption wavelength.

19. The system in accordance with claim 16, wherein the system is configured correct the concentration measurements of NOx and ammonia by subtracting out the concentration measurement of water vapor made using the absorption wavelength for water vapor within the range of between approximately 0.9 and 1.5 µm.

20. The system in accordance with claim 1, wherein the control unit controls the rate at which the reductant injects reductant into the stream of combustion exhaust based upon the measured concentration levels of nitrogen oxide and the reductant.

21. The system in accordance with claim 8, wherein:
the reductant injector comprises means for injecting the reductant in a spatially controlled manner; and
the spatially controlled injection of reductant is based upon the calculated spatial distribution data relating to the spatial distribution of the measured concentration levels of nitrogen oxide and ammonia.

22. The system in accordance with claim 21, wherein means for injecting the reductant in a spatially controlled manner comprises at least one of: 1) a plurality of reductant injection nozzles that project into the stream of the combustion exhaust so that a plurality of reductant injection locations are provided; 2) a plurality of reductant injection nozzles that are spaced around the periphery of the downstream conduit; and 3) both; and
wherein means for injecting the reductant in a spatially controlled manner comprises injecting higher levels of the reductant in areas with higher concentration levels of nitrogen oxide and injecting lower levels of the reductant in areas with lower concentration levels of nitrogen oxide.

23. A system for the monitoring and/or controlling emission levels of nitrogen oxide and a reductant from a stream of combustion exhaust from an internal combustion engine, wherein the internal combustion engine includes a selective catalytic reduction unit disposed in the stream of combustion exhaust between an upstream conduit that directs the stream of combustion exhaust to the selective catalytic reduction unit and a downstream conduit that directs the stream of combustion exhaust away from the selective catalytic reduction unit, the selective catalytic reduction unit having a catalyst that is configured to catalytically reduce nitrogen oxides contained in the combustion exhaust to elemental nitrogen in the presence of a reductant and oxygen, and wherein the internal combustion engine further includes a reductant injector that injects the reductant into the flow of combustion exhaust upstream of the selective catalytic reduction unit, the system comprising:
a first tunable diode laser spectroscopy unit that is disposed in the downstream conduit and configured to measure the concentration levels of at least nitrogen oxide and the reductant in the stream of combustion exhaust;
a second tunable diode laser spectroscopy unit that is disposed upstream of the reductant injector in the upstream conduit; and
a control unit;
wherein the first tunable laser spectroscopy unit and the second tunable laser absorption spectroscopy unit are each configured to measure the concentration level of at least nitrogen oxide in the stream of combustion exhaust and provide timely data to the control unit relating to the measured concentration level of nitrogen oxide;
wherein the first tunable laser spectroscopy unit is configured to measure the concentration level of the reductant in the stream of combustion exhaust and to provide timely data to the control unit relating to the measured concentration level of the reductant; and
wherein timely data comprises data that comprises a lag time of less than 1 second.

* * * * *